_United States Patent_ [19]

Shimizu et al.

[11] Patent Number: 4,495,285

[45] Date of Patent: Jan. 22, 1985

[54] PLASMINOGEN ACTIVATOR DERIVATIVES

[76] Inventors: Kimihiro Shimizu, Yoshikawa-danchi 4-16-102, Yoshikawa-machi, Kitakatsushika-gun, Saitama-ken; Tsuguji Nakahara, 6-21-6, Megurohonmachi, Meguro-ku, Tokyo; Taketoshi Kinoshita, Satsuki-so, Noborito 15-30, Koshigaya-shi, Saitama-ken, all of Japan

[21] Appl. No.: 437,009

[22] Filed: Oct. 27, 1982

[30] Foreign Application Priority Data

Oct. 30, 1981 [JP] Japan ............................ 56-172908

[51] Int. Cl.³ .................. C12N 9/72; C12N 9/48; C12N 11/06
[52] U.S. Cl. ............................ 435/215; 435/212; 435/181
[58] Field of Search ................... 435/181, 212, 215

[56] References Cited

U.S. PATENT DOCUMENTS 4,179,337  12/1979  Davis et al. ................... 435/181
4,349,630   9/1982  Maximenko et al. .......... 435/215 X

OTHER PUBLICATIONS

Kenneth J. Weider et al., "Some Properties of Polyethylene Glycol: Phenylalanine Ammonia–Lyase Adducts", J. Biol. Chem. 254 (24): 12579–12587 (1979).
Stephen Davis et al., "Hypouricaemic Effect of Polyethylene Glycol Modified Urate Oxidase", The Lancet, Aug. 8: 281–283 (1981).
Kenneth V. Savoca et al., "Preparation of a Non-immunogenic Arginase by the Covalent Attachment of Polyethylene Glycol", Biochim. Biophys. Acta, 578: 47–53 (1978).
Peter S. Pyatak et al., "Preparation of a Polyethylene Glycol: Superoxide Dismutase Adduct, and an Examination of its Blood Circulating Life and Anti–inflammatory Activity", Res. Commun. Chem. Pathol. Pharmacol., 29(1): 113–127 (1980).
Robert H. L. Chen et al., "Properties of Two Urate Oxidases Modified by the Covalent Attachment of Poly(Ethylene Glycol)", Biochim., Biophys. Acta, 660: 293–298 (1981).
Abraham Abuchowski et al., "Immunosuppressive Properties and Circulating Life of Achromobacter Glutaminase–Asparaginase Covalently Attached to Polyethylene Glycol in Man", Cancer Treat. Rep., 65: 11–12 (1981).

_Primary Examiner_—Lionel M. Shapiro

[57] ABSTRACT

A derivative of a human-originated non-immunogenic plasminogen activator is disclosed which comprises at least one polyalkylene glycol attached with at least one coupling agent to amino acid side chains of said plasminogen activator, said polyalkylene glycol having a molecular weight of 200–20,000 and optionally containing one or more alkyl and/or alkanoyl groups as substituents. Also disclosed are a process for producing such derivative and a thrombolytic agent containing such derivative.

17 Claims, 7 Drawing Figures

4,495,285

PLASMINOGEN ACTIVATOR DERIVATIVES

BACKGROUND OF THE INVENTION

1. Field of the Invention

This invention relates to novel derivatives of human-originated non-immunogenic plasminogen activators, and more particularly to such a derivative comprising at least one polyalkylene glycol attached with at least one coupling agent to amino acid side chains of a plasminogen activator of the type described above, the polyalkylene glycol having a molecular weight in the range of 200–20,000 and optionally containing one or more alkyl and/or alkanoyl groups as substituents. Further, the invention is concerned with a process for producing such novel derivative and with a thrombolytic agent containing such novel derivative.

2. Description of the Prior Art

It is known that human tissues contain a variety of substances which activate plasminogen into a fibrinolytic enzyme or plasmin. Among such known substances, the most representative is a plasminogen activator, i.e. urokinase, which is formed in the kidney tissue and excreted into urine. Urokinase may be obtained by isolation and purification from human urine, tissue culture or genetic engineering. As fibrinolytic enzyme activators which have nowadays found widespread commercial utility, there exist proteins originated from hemolytic Streptococcus and urokinase which is an enzyme originated from human urine. In view of its non-immunogenic behavior to humans, urokinase resulting from such source is favorably employed for clinical application. Urokinase originated from human urine is believed to contain both high molecular weight urokinase (molecular weight: 54,000) and low molecular weight urokinase (molecular weight: 33,000). Urokinase has been used, in recent years, as a thrombolytic agent or an adjuvant for carcinostatic substances, and its consumption for clinical application is increasing year by year.

However, urokinase is unstable under certain conditions since it is an enzyme and loses its enzymatic activity, for example, in the course of extraction, isolation and purification from a urokinase-bearing raw material, for example, urine; during the lyophilization processing in preparing dosable formulations; during the heat treatment for deactivating viruses; or when it is placed in a diluted state in a dripping bottle and kept for a prolonged time period in such a diluted state at room temperature for clinical application. This physically unstable nature of urokinase has created a serious problem in preparing and formulating urokinase on an industrial scale or in actually using the same for clinical purposes. Human albumin has been employed as an additive to urokinase so as to improve its stability. However, this can be by no means a break-through solution to the problem just discussed because pure albumin, i.e. a globulin fraction, is difficult to obtain without immunogenic contamination; pure albumin is expensive; albumin and urokinase form a complex of a high molecular weight under virus deactivating conditions in which urokinase is subjected to heat treatment at 60° C. for 10 hours together with albumin added to stabilize urokinase; and such stabilizer if added may be effective to a certain extent for protecting urokinase from losing its enzymatic activity upon the lyophilization but cannot prevent its loss of activity upon actual clinical use.

The physiological activity of urokinase when administered intravenously to living bodies is promptly retarded by protease inhibitors present in blood ($\alpha_2$-macroglobulin, and $\alpha_2$-plasmin inhibitors and the like), and the metabolic rate of urokinase per se is very high, resulting in extremely shortened half-life which does not exceed even several minutes. Nothing has been heretofore proposed to solve the problem of short half-life of urokinase in blood.

The present inventors have carried out extensive research with a view toward developing novel derivatives of human-originated non-immunogenic plasminogen activators which will overcome the above-noted drawbacks of the prior art techniques. As a result, they have succeeded in finding novel plasminogen activator derivatives which are stable and hardly retarded by inhibitors present in blood and hence achieve prolonged half-life in blood, thereby leading to the present discovery.

SUMMARY OF THE INVENTION

An object of the present invention is to provide a novel derivative of a human-originated non-immunogenic plasminogen activator which is stable and exhibits prolonged fibrinolytic activity when administered to living bodies.

Another object of the invention is to provide a process for preparing the novel plasminogen activator derivative.

A further object of the invention is to provide a therapeutically acceptable thrombolytic agent comprising the novel plasminogen activator derivative.

These and other objects and advantages of the invention can be attained by the provision of a derivative of a human-originated non-immunogenic plasminogen activator, comprising at least one polyalkylene glycol attached with at least one coupling agent to amino acid side chains of the plasminogen activator, the polyalkylene glycol having a molecular weight in the range of 200–20,000 and optionally containing one or more alkyl and/or alkanoyl groups as substituents.

BRIEF DESCRIPTION OF THE DRAWINGS

A more complete appreciation of the present invention and many of the attendant advantages thereof will be readily obtained as the invention becomes better understood by reference to the following detailed description when considered in connection with the accompanying drawings, wherein.

DESCRIPTION OF THE PREFERRED EMBODIMENTS

Figure 1:
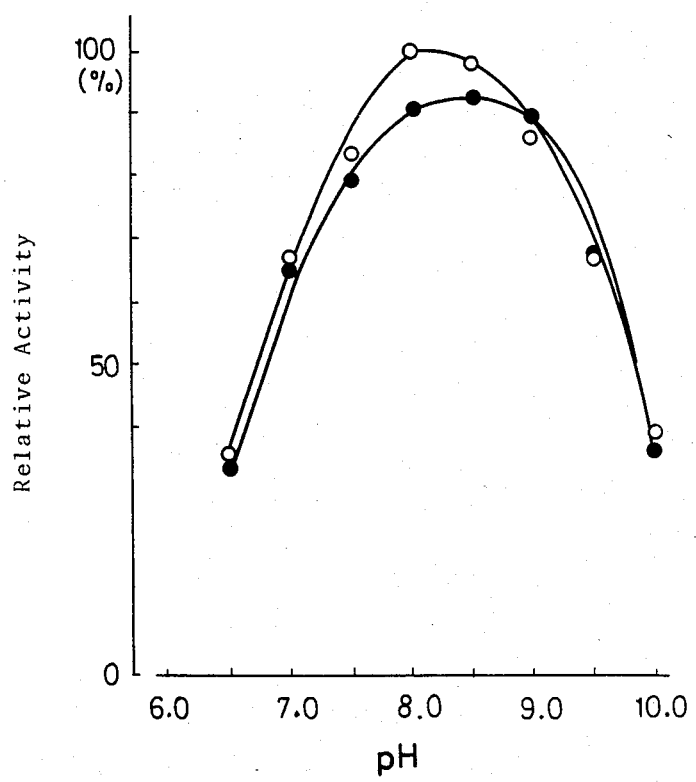
FIG. 1 shows the optimum pH ranges of modified high molecular weight urokinase (PEG-DCT-UK) and unmodified high molecular weight urokinase (molecular weight: 54,000) as measured in terms of the amidase activity with a synthetic substrate (S-2444), where the open circles correspond to PEG-DCT-UK and the closed circles to unmodified urokinase.

By the term "human-originated non-immunogenic plasminogen activator" as used herein are encompassed not only urokinase but also tissue plasminogen activators obtained from human tissues such as uterine, tumor and the like. These human tissue plasminogen activators also contain those obtained by tissue culture or genetic engineering. It should be noted that no limitations are imposed on the molecular weights of these activators so long as they are obtained in the above-described manner. For example, as urokinase which is a plasminogen activator originated from human urine, high molecular weight urokinase (molecular weight: 54,000) and low molecular weight urokinase (molecular weight: 33,000) may be used solely or in combination.

Suitable polyalkylene glycols which may be used in the invention include a polyethylene glycol and a polypropylene glycol. In the case of the polypropylene glycol, both straight-chain polypropylene glycols such as those represented by $HO[CH(CH_3)CH_2O]_nH$ and branched-chain polypropylene glycols such as those represented by $CH_3CH_2C-\{CH_2O[CH_2CH(CH_3)O]_nH\}_3$ or $H[OCH(CH_3)CH_2]_n\ OCH\{CH_2[OCH_2CH-(CH_3)]_nOH\}_2$.

The molecular weights of the polyalkylene glycols may range from 200 to 20,000. Particularly preferred molecular weights are in the range of 500–10,000.

The polyalkylene glycols each may optionally contain one or more alkyl and/or alkanoyl groups as substituent groups. Typical examples of the alkyl groups are methyl, ethyl, propy, stearyl and the like. Typical examples of the alkanoyl groups are acetyl, propionyl, stearoyl and the like. As a preferred polyalkyene glycol, an unsubstitued or methyl-substituted polyalkylene glycol is useful.

Suitable coupling agents which may be used in the invention and are adapted to attach a polyalkylene glycol to a non-immunogenic plasminogen activator, for example, urokinase, include those capable of reacting with amino acid side chains of the protein to be modified and forming chemical bonds therebetween, for example, acyl azide, cyanuric halides, p-diazoniumbenzyl ether, 3-(p-diazoniumphenoxy)-2-hydroxypropyl ether, dihalogenosuccinic anhydride and the like. The following partial formulae may be given as examples of the coupling structures between a polyalkylene glycol and urokinase through these coupling agents.

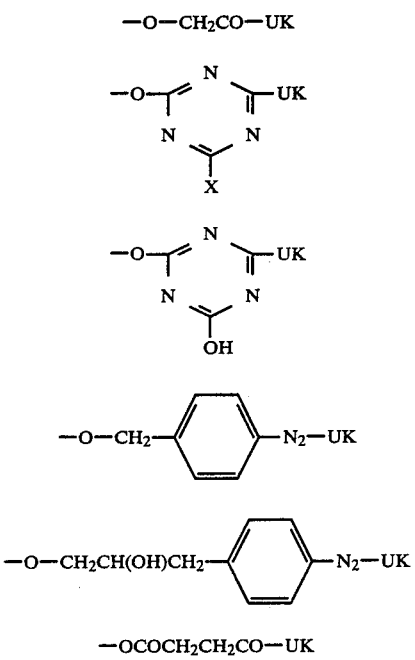

wherein X is a halogen atom, and UK is a residual part of the urokinase molecule.

The novel urokinase derivative according to the invention can be prepared by reacting a coupled product of at least one corresponding polyalkylene glycol and at least one coupling agent with urokinase, the polyalkylene glycol having a molecular weight in the range of 200–20,000 and optionally containing one or more alkyl and/or alkanoyl groups as substituents.

Typical examples of the polyalkylene glycol-coupling agent coupled product include polyalkylene glycol-4,6-dichloro-1,3,5-triazine, polyalkylene glycol-4,6-difluoro-1,3,5-triazine, polyalkylene glycol-4-chloro-6-hydroxy-1,3,5-triazine, polyalkyene glycol-$\beta$-(bromocarbonyl)monopropionate, polyalkylene glycol-azidocarbonyl methyl ether, polyalkylene glycol-(p-diazoniumbenzyl) ether, polyalkylene glycol-3-(p-diazoniumphenoxy)-2-hydroxypropyl ether and the like.

When reacting the polyalkylene glycol-coupling agent coupled product with urokinase, it is necessary to choose such reaction conditions that the enzymatic activity is held to a minimum loss. Namely, it is desirable to carry out the reaction at low temperatures, for example, at a temperature of 0° C. to room temperature in an aqueous solution such as a buffer. Preferred reaction time may range from several minutes to 5 hours. The pH of the buffer is preferably within such a range that the enzymatic activity of urokinase is not lowered, namely, 2–10, preferably 5–9. However, the preferred pH range may vary depending on the reactivity of each coupling agent employed and/or the nature of an amino acid residue. The modification degrees of amino acid side chains of the plasminogen activator can be controlled by changing the concentration of the polyalkylene glycol activated with the coupling agent in a reaction medium. By way of illustration, monomethyl ether polyethylene glycol-4,6-dichloro-1,3,5-triazine having an average molecular weight of 5,000 was reacted at pH 7.0 with high molecular weight urokinase to obtain novel urokinase derivatives, while changing the concentration of the former reactant to 0.4, 4.0 and 6.0 mM, respectively. Unmodified $\epsilon$-amino groups of lysine of the resultant urokinase derivatives were quantitatively determined using sodium 2,4,6-trinitrobenzenesulfonate. Their modification degrees were investigated on the basis of the results obtained by the quantitative analyses. The modification percentages of the $\epsilon$-amino groups of lysine, which were reactive with sodium 2,4,6-trinitrobenzenesulfonate, were 6–7% at 0.4 mM, about 40% at 4.0 mM and about 60% at 6.0 mM. In addition, the molecular weights of these reaction products were determined by SDS polyacryl amide gel electrophoresis. The average molecular weights of the reaction products were about 60,000 at 0.4 mM and about 120,000 at 4.0 mM. This finding is substantially in conformity with the results obtained above by the quantitative analyses of the $\epsilon$-amino groups of lysine. Accordingly, it is necessary to conduct the reaction between the polyalkylene glycol activated with the coupling agent and the plasminogen activator at a high pH level and at a high concentration of the former reagent when increased modification degrees of the plasminogen activator are desired. On the other hand, where decreased modification degrees are preferable, the reaction should be effected at a relatively low pH level and at a low concentration of the coupled product. The modification degrees may of course be changed by controlling the reaction time. By suitably combining these reaction conditions, it is possible to obtain the intended novel plasminogen activator derivatives which are stable and have prolonged fibrinolytic activities.

The polyalkyene glycol activated with the coupling agent can be obtained in the following manner. A terminal-substituted polyalkylene glycol-4,6-dihalogeno-1,3,5-triazine is obtained by reacting its corresponding mono-substituted polyalkylene glycol with a cyanuric halide in an anhydrous solvent and in the presence of a base. A polyalkylene glycol-4-halogeno-6-hydroxy-1,3,5-triazine is formed by first reacting its corresponding polyalkylene glycol with cyanuric halide and then treating the resultant reaction product with water. A polyalkylene glycolacetoazide is formed by reacting an anion of its corresponding polyalkylene glycol with ethyl chloroacetate, followed by treating the reaction product with hydrazine, and finally activating the resulting hydrazide with nitrous acid. A polyalkylene glycol-p-diazoniumbenzyl ether or a polyalkylene glycol-3-(p-diazoniumphenoxy)-2-hydroxypropyl ether is obtained by reacting its corresponding polyalkylene glycol with p-nitrobenzyl chloride or p-nitrophenyl glyceryl ether and, after reducing the nitro group into an amino group, diazotizing the resultant product with nitrous acid.

After completion of the reaction of the polyalkylene glycol activated with the coupling agent and the plasminogen activator, the isolation and purification of the reaction product may be effected in a biochemical manner known per se in the art, for example, by using singly or in combination gel filtration, dialysis, ion-exchange chromatography, affinity chromatography and the like. Preferably, the conjugate is kept as a solution containing a buffer or a physiological salt, by freezing the solution below $-20°$ C., or by lyophilizing the solution.

Figure 2:
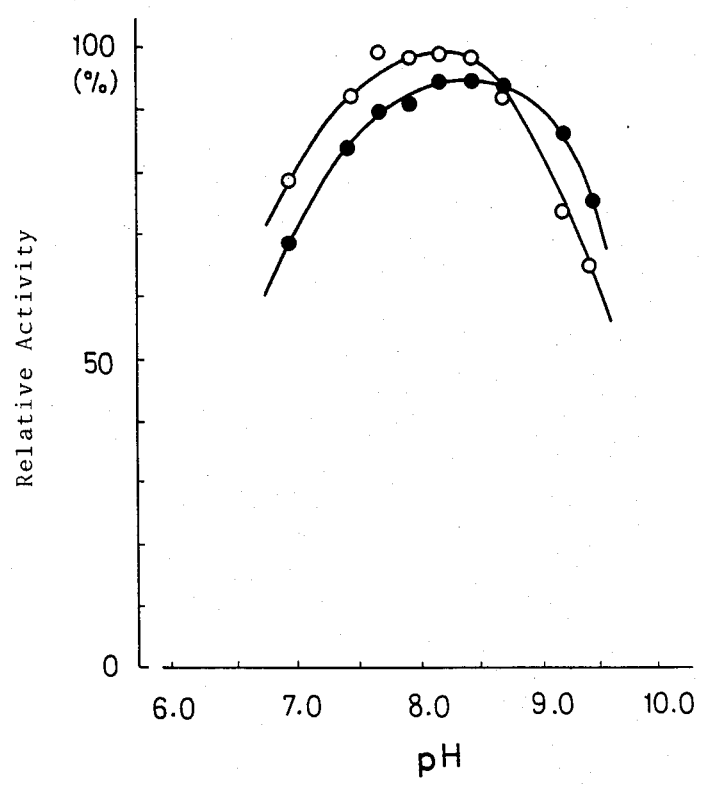
FIG. 2 shows the optimum pH ranges of modified low molecular weight urokinase (PEG-DCT-L-UK) and unmodified low molecular weight urokinase (molecular weight: 33,000) as measured in terms of the amidase activity with S-2444, where the open circles correspond to PEG-DCT-L-UK and the closed circles to unmodified urokinase.

The optimum pH levels for the novel urokinase derivatives prepared above vary depending on the molecular weights and types of polyalkylene glycols employed, the types of coupling agents employed, the modification degrees of urokinase, the modification conditions and the measurement conditions such as substrates used. When measured in terms of the amidase activity using a synthetic substrate S-2444, the optimum pH level is within the range of about 8 to 9. In the case of high molecular weight urokinase modified by reaction with monomethyl ether polyethylene glycol-4,6-dichloro-1,3,5-triazine having an average molecular weight 5,000 at pH 7.0 and at a temperature of $0°$ C. for 3 hours, while using the latter reactant at a concentration of 4.0 mM (hereinafter abbreviated as PEG-DCT-UK), the optimum pH as measured in terms of the amidase activity is 8.2 as shown in FIG. 1. The optimum pH of low molecular weight urokinase modified under the same conditions (hereinafter abbreviated as PEG-DCT-L-UK) is, as measured in terms of the amidase activity, 8.2 as shown in FIG. 2.

Figure 3:
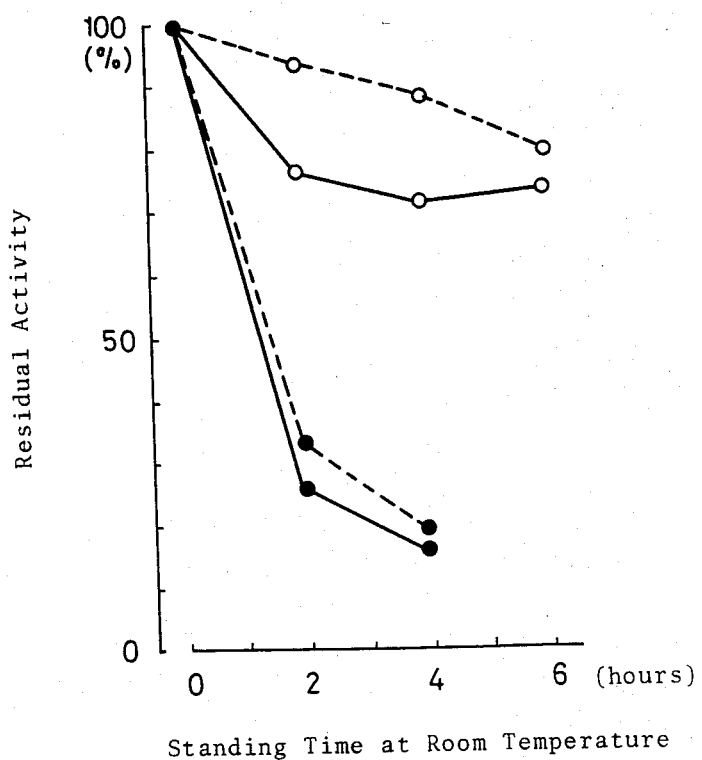
FIG. 3 diagrammatically shows the stability of PET-DCT-UK and unmodified urokinase at room temperature in either physiological saline or a Ringer solution, where the solid and broken lines indicate the physiological saline and the Ringer solution, respectively, and where the open circles correspond to PEG-DCT-UK and the closed circles to unmodified urokinase.

The novel urokinase derivatives according to the invention have extremely enhanced stability compared with unmodified urokinase. For instance, FIG. 3 shows the results of the residual urokinase activity obtained relative to the passage of time when urokinase was diluted with a Ringer solution or a physiological solution to such a concentration as used by dripping administration for clinical application and then allowed to stand at room temperature. As a result, it has been found that PEG-DCT-UK dissolved at a concentration of 105.3 iu/ml in the Ringer solution maintains an activity of 73.4% at the initiation of the experiment even after 6 hours. In addition, PEG-DCT-UK retains an initial activity of 79.4% in the physiological saline. On the other hand, unmodified urokinase dissolved at a concentration of 76.1 iu/ml in a Ringer solution keeps only 33.3% in its initial activity even after 2 hours. In a physiological saline, the residual activity is as low as 26.3%.

Figure 4:
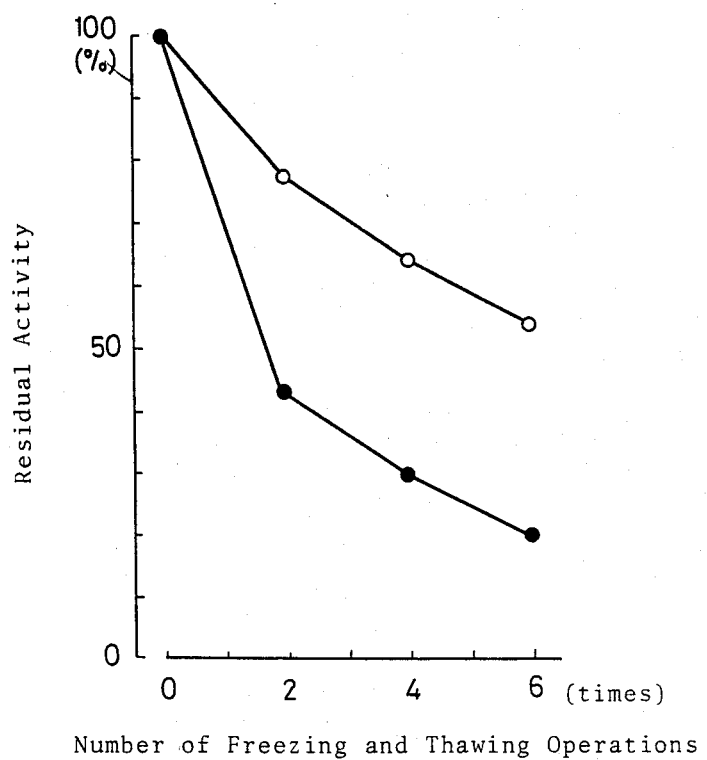
FIG. 4 shows the stability of PEG-DCT-L-UK and unmodified urokinase (molecular weight: 33,000) against freezing, followed by thawing operation repeated 2, 4 and 6 times, where the open circles correspond to PEG-DCT-L-UK and the closed circles to unmodified urokinase.

FIG. 4 illustrates the results obtained by comparing the stability of PEG-DCT-L-UK and unmodified low molecular weight urokinase, both in the course of freezing, followed by thawing operation. The results confirm that the superb stability of PEG-DCT-L-UK is attained even under such conditions.

Figure 5:
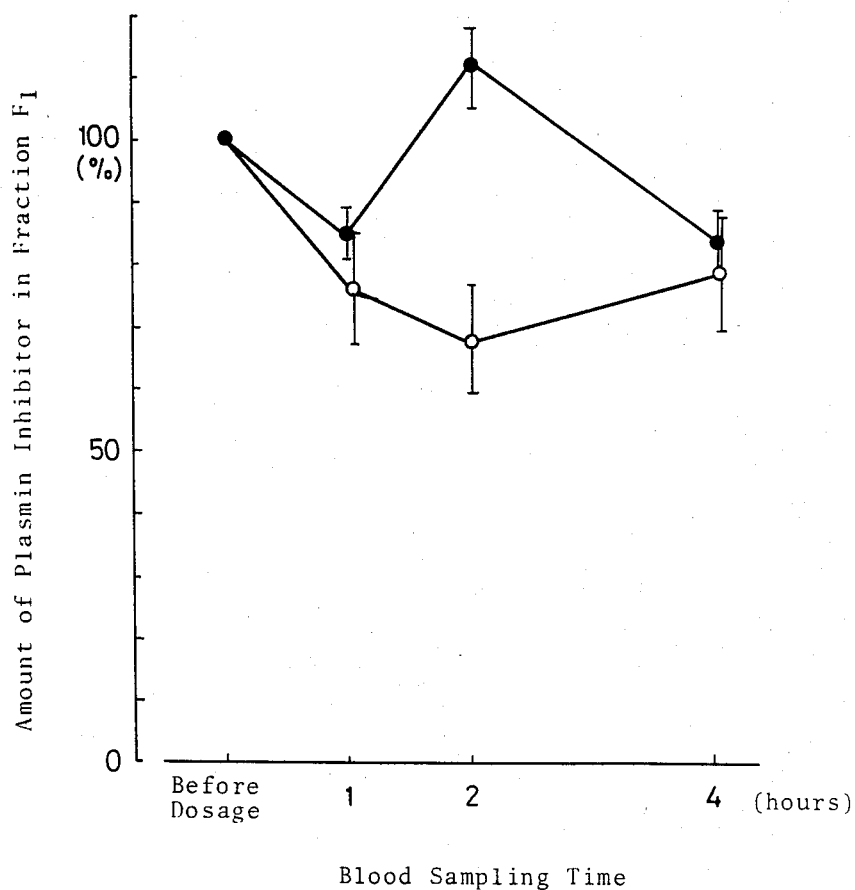
FIG. 5 shows the varied amounts, as a function of time, of a plasmin inhibitor in a plasma fraction $F_1$ of each of two groups of healthy rabbits, one group administered with PEG-DCT-UK and the other group with unmodified urokinase (molecular weight: 54,000), where the open circles correspond to the PEG-DCT-UK-administered group and the closed circles to the unmodified urokinase-administered group.
Figure 6:
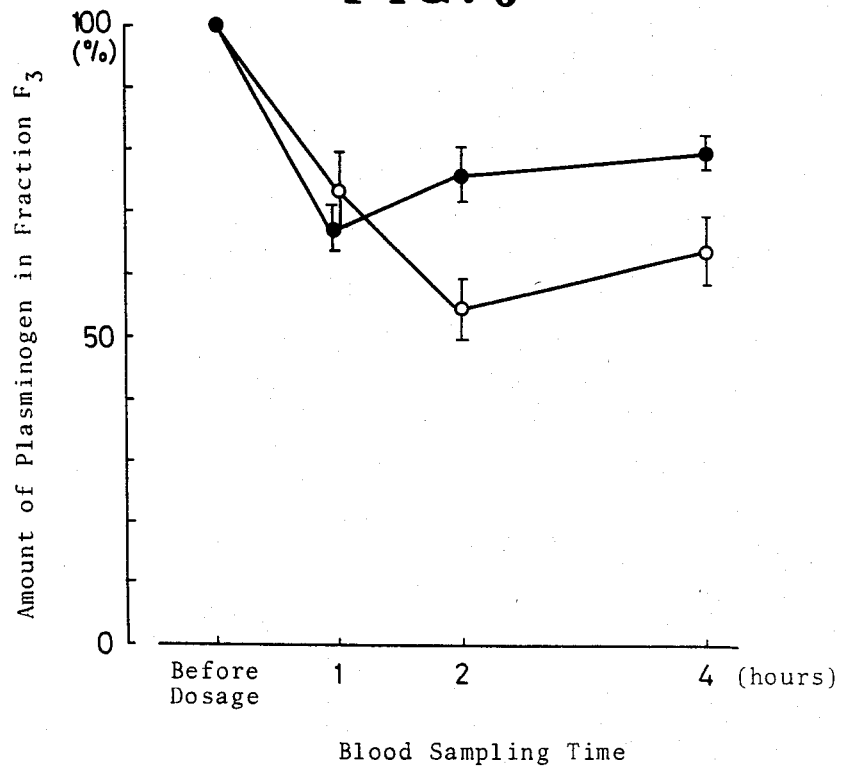
FIG. 6 shows the varied amounts, as a function of time, of plasminogen in a plasma fraction $F_3$ of each of two groups of healthy rabbits, one group administered with PEG-DCT-UK and the other group with unmodified urokinase (molecular weight: 54,000), where the open circles correspond to the PEG-DCT-UK-administered group and the closed circles to the unmodified urokinase-administered group.
Figure 7:
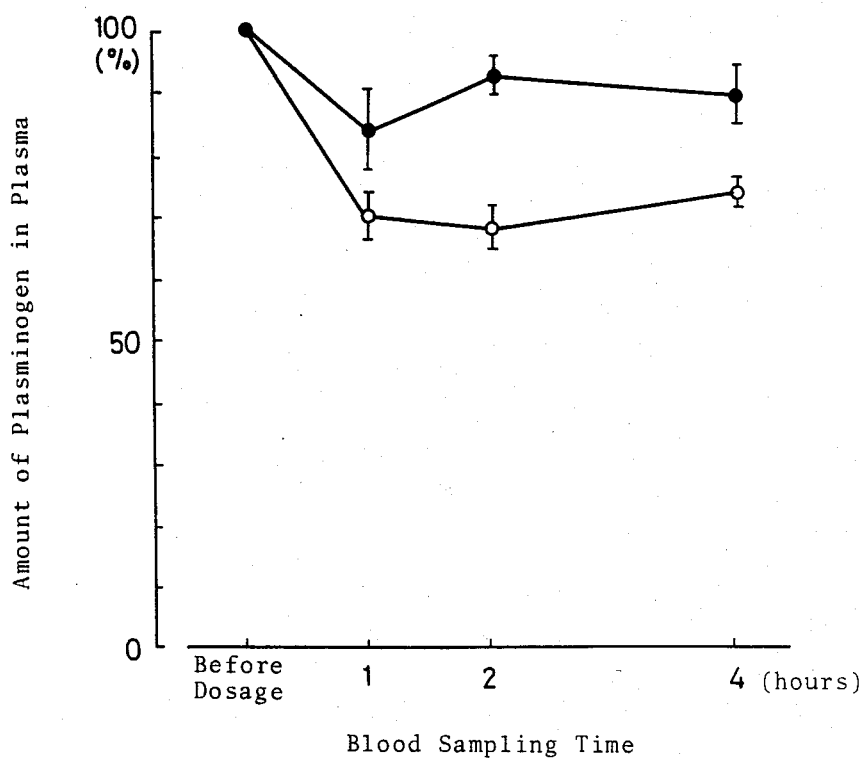
FIG. 7 shows the varied amounts, as a function of time, of plasminogen in a plasma fraction $F_3$ of each of two groups of healthy rabbits, which plasma was treated with an acid and then with a base to inactivate a plasmin inhibitor, one group administered with PEG-DCT-UK and the other group with unmodified urokinase (molecular weight: 54,000), where the open circles correspond to the PEG-DCT-UK-administered group and the closed circles to the unmodified urokinase-administered group.

Furthermore, the novel urokinase derivatives according to the invention have prolonged urokinase activities in blood as compared with unmodified urokinase. For example, the effectiveness of urokinase was investigated by administering 8,000 iu/kg of each of PEG-DCT-UK and modified urokinase to healthy rabbits by intravenous injection, sampling blood periodically before the dosage and after the lapse of 4 hours, and measuring the amounts of the plasmin inhibitor and plasminogen present in the citrated plasma. The results are shown in FIGS. 5, 6 and 7. From these results, it has been confirmed that PEG-DCT-UK alters to a substantial extent biochemical parameters such as a plasmin inhibitor and plasminogen and maintains the parameters at lowered values for an extended period of time as compared with unmodified urokinase.

Therefore, the novel urokinase derivatives according to the invention are excellent plasminogen activators which, while retaining plasminogen-activating potency as unmodified urokinase does, have surmounted the shortcomings of urokinase such as poor stability and short half-life in blood.

The novel urokinase derivatives according to the invention may be used as pharmaceutical products for the treatment of a variety of diseases stemmed from hypercoagulability of blood such as arterial and venous thromboses, coronary artery clotting, myocardial infarction, intracerebral infarction, pulmonary embolism, nephritis and the like. These urokinase derivatives can be suitably administered by intravenous injection or dripping or by an oral route. The intravenous injection is particularly preferred. As dosable forms, preferably usable is a lyophilized form. When supplied either in a neat state or with a physiological salt such as a salt of a Ringer solution or sodium chloride, the lyophilized products may be used for clinical application by dissolution with sterile distilled water or further dilution with sterile distilled water in order to adjust their osmotic pressure, prior to the actual use. Since the novel urokinase derivatives according to the invention are stable, they do not require a stabilizer such as albumin. However, the addition of such a stabilizer does not cause any problem or inconvenience. An excipient may also be added in subjecting the novel urokinase derivatives to lyophilization.

The above description generally describes the present invention. A more complete understanding can be obtained by reference to the following examples which are provided for purposes of illustration only and are not intended to be limiting. The modification procedure may be carried out in any one of the preparation steps of plasminogen activators.

EXAMPLE 1

Monomethyl ether polyethylene glycol-4,6-dichloro-1,3,5-triazine

Polyethylene glycol monomethyl ether having an average molecular weight of 5,000 (25.0 g; 0.05 mole) was dissolved with warming in dry benzene (200 ml). After cooling the resultant solution to room temperature, anhydrous sodium carbonate (5.0 g) and cyanuric chloride (2.75 g; 0.015 mole) were added, and the mixture was stirred overnight at room temperature. After completion of the reaction, the reaction mixture was filtered, and petroleum ether (600 ml) was added to the filtrate. The resulting precipitate was collected by suction filtration and washed with a small amount of petroleum ether. The precipitate was purified by being reprecipitated three times from dry benzene and petroleum ether to remove excess cyanuric chloride, thereby stoichiometrically obtaining monomethyl ether polyethylene glycol-4,6-dichloro-1,3,5-triazine as white powder. The product after hydrolyzed showed qualitative reaction characteristics of chlorine ions (AgNO$_3$).

Similarly, polyethylene glycol monomethyl ethers having average molecular weights of 550, 700, 2,000 and 20,000, respectively, were each reacted with cyanuric chloride to stoichiometrically obtain monomethyl ether polyethylene glycol-4,6-dichloro-1,3,5-triazines having the corresponding average molecular weights.

EXAMPLE 2

Monomethyl ether polyethylene glycol-4,6-dichloro-1,3,5-triazines (average molecular weights of their polyethylene glycol moieties: 10,000 and 15,000)

Polyethylene glycol monomethyl ether having an average molecular weight of 10,000 (25.0 g; 0.025 mole) was taken up with warming in dry benzene (200 ml). After cooling the resultant solution, anhydrous sodium carbonate (2.5 g) and cyanuric chloride (1.38 g; 0.0075 mole) were added. The resultant mixture was stirred overnight at 33° C. After completion of the reaction, undissolved matter was removed by filtration. The filtrate was added with n-hexane (about 600 ml) to induce reprecipitation. Dry benzene (100 ml) was added to the precipitate which was then warmed and dissolved. n-Hexane (500 ml) was then added to induce reprecipitation. This procedure was repeated three times. The thus obtained precipitate was dried overnight at 50° C. in vacuo, thereby stoichiometrically obtaining monomethyl ether polyethylene glycol-4,6-dichloro-1,3,5-triazine (the average molecular weight of the polyethylene glycol moiety: 10,000) as while powder. Polyethylene glycol monomethyl ether having an average molecular weight of 15,000 was similarly reacted with cyanuric chloride to stoichiometrically obtain monomethyl ether polyethylene glycol-4,6-dichloro-1,3,5A-triazine (the average molecular weight of the polyethylene glycol moiety: 15,000).

EXAMPLE 3

Monostearyl ether polyethylene glycol-4,6-dichloro-1,3,5-triazine

Polyethylene glycol monostearyl ether having an average molecular weight of 3,200 (16.0 g; 0.005 mole) was dissolved in dry benzene (200 ml), followed by the addition of anhydrous sodium carbonate (5.0 g) and cyanuric chloride (2.75 g; 0.015 mole) under stirring. The resultant mixture was stirred overnight at room temperature. After completion of the reaction, undissolved matter was removed by filtration. The filtrate was added with n-hexane (about 600 ml) to induce reprecipitation. Dry benzene (100 ml) was added to the precipitate to dissolve the latter. n-Hexane (500 ml) was added to induce reprecipitation. This procedure was repeated three times, thereby stoichiometrically obtaining monostearly ether polyethylene glycol-4,6-dichloro-1,3,5-triazine (the average molecular weight of the polyethylene glycol moiety: 3,200) as white powder.

EXAMPLE 4

Polyethylene glycol-4-chloro-6-hydroxy-1,3,5-triazine

Polyethylene glycol having an average molecular weight of 6,000 (33.6 g) was dissolved with warming in dry benzene (150 ml). After cooling the resultant solution, anhydrous sodium carbonate (1.6 g) and cyanuric chloride (0.74 g) were added, and the resultant mixture was stirred overnight at room temperature. Thereafter, water (1.0 ml) was added, followed by stirring the mixture at room temperature for 6 hours and then at 40° C. for an overnight period. Undissolved matter was removed by centrifuge (2,000 ppm; 10 minutes), and the supernatant was subjected to condensation under reduced pressure. The residue was taken up with warming in dry benzene, and the solvent was then evaporated. This procedure was further repeated twice. The residue was dried under reduced pressure, thereby obtaining polyethylene glycol-4-chloro-6-hydroxy-1,3,5-triazine (the average molecular weight of the polyethylene glycol moiety: 6,000).

Polyethylene glycols having different average molecular weights of 1,000 and 4,000 were each reacted in the same manner as above with cyanuric chloride and water, resulting in the stoichiometric formation of polyethylene glycol-4-chloro-6-hydroxy-1,3,5-triazines having their corresponding average molecular weights.

EXAMPLE 5

Stearoylpolyethylene glycol-4,6-dichloro-1,3,5-triazine

Polyethylene glycol monostearate having an average molecular weight of 2,700 (6.765 g) was dissolved in anhydrous benzene (100 ml), followed by the addition of anhydrous sodium carbonate (2.5 g). While stirring the resultant mixture, cyanuric chloride (1.38 g) was further added. The resulting mixture was stirred overnight at room temperature and then filtered. The filtrate was concentrated under reduced pressure, and the residue was dried under reduced pressure, thereby stoichiometrically obtaining stearoylpolyethylene glycol-4,6-dichloro-1,3,5-triazine (the average molecular weight of the polyethylene glycol moiety: 2,700) as a white waxy substance.

EXAMPLE 6

Polypropylene glycol-4-chloro-6-hydroxy-1,3,5-triazine

Polypropylene glycol having an average molecular weight of 1,000 (4.0 g) was taken up in anhydrous benzene (50 ml), followed by the addition of anhydrous sodium carbonate (1.27 g). Cyanuric chloride (0.552 g) was further added with stirring. After stirring the resultant mixture overnight at room temperature, water (1 ml) was added. The mixture was stirred at room temperature for further 6 hours. The reaction mixture was filtered, and the filtrate was concentrated under reduced pressure. The residue was added with anhydrous benzene and anhydrous sodium sulfate. The mixture was thereafter stirred at room temperature for 10 minutes. After filtration of the mixture, the solvent was evaporated from the filtrate. The residue was dried under reduced pressure, thereby stoichiometrically obtaining polypropylene glycol-4-chloro-6-hydroxy-1,3,5-triazine (the average molecular weight of the polypropylene glycol moiety: 1,000) as colorless viscous oil.

Following the same procedure as described above, there were obtained a polypropylene glycol-4-chloro-6-hydroxy-1,3,5-triazine (the average molecular weight of the polypropylene glycol moiety: 4,000) and another polypropylene glycol-4-chloro-6-hydroxy-1,3,5-triazine (the average molecular weight of the polypropylene glycol moiety: 10,000).

The polypropylene glycols employed in the above examples were of a straight-chain type, namely, those respresented by the formula $HO[CH(CH_3)CH_2O]_nH$.

EXAMPLE 7

Polypropylene glycol-4-chloro-6-hydroxy-1,3,5-triazine

Following the same procedure as in Example 1, polypropylene glycol-4-chloro-6-hydroxy-1,3,5-triazine (the average molecular weight of the polypropylene glycol moiety: 4,000) was stoichiometrically obtained as a white substance from polypropylene glycol having an average molecular weihgt of 4,000 (8.0 g), anhydrous benzene (80 ml), anhydrous sodium carbonate (0.636 g) and cyanuric chloride (0.368 g).

The polypropylene glycol used in this example was of a branched-chain type, namely, those represented by the formula $CH_3CH_2C\{CH_2O[CH_2CH(CH_3)O]_nH\}_3$.

Furthermore, using polypropylene glycol represented by the formula,

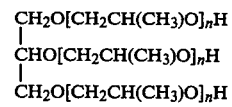

and having an average molecular weight of 3,000, there was obtained polypropylene glycol-4-chloro-6-hydroxy-1,3,5-triazine (the average molecular weight of the polypropylene glycol moiety: 3,000).

EXAMPLE 8

Monomethyl ether polyethylene glycol methoxycarbohydrazide

Polyethylene glycol monomethyl ether having an average molecular weight of 5,000 (13.3 g; 0.0027 mole) was taken up in anhydrous tetrahydrofuran (400 ml) under nitrogen. A small amount of diphenylacetic acid was added as an indicator, and n-butyl lithium was dropped under ice-cooling until the reaction solution turned to pale yellow. Thereafter, ethyl chloroacetate (5 ml; 0.047 mole) was dropped at room temperature, and the resultant solution was stirred overnight and then refluxed for one hour. After completion of the reaction, the solvent was driven off under reduced pressure, and the residue was taken up in aqueous acetone (200 ml). The resultant solution was treated with charcoal. After filtration and subsequent concentration of the filtrate, benzene was added. After removing water by azeotropic distillation, the residue was reprecipitated from benzene and n-hexane to obtain yellowish powder. The thus obtained powder was dissolved in methanol (150 ml) and then added with hydrazine hydrate (15 ml). The mixture was heated overnight under reflux conditions. After driving off the solvent under reduced pressure, water (150 ml) was added, and excess hydrazine was removed by azeotropic distillation. Water, still remaining in the residue, was removed azeotropically together with benzene. The residue was again dissolved in benzene and dried with anhydrous sodium sulfate. Thereafter, the solvent was driven off, and the residue was dissolved in warm benzene. The benzene solution was treated with charcoal and then concentrated. The reaction product was reprecipitated twice from benzene and n-hexane, treated with charcoal again and with silica gel and then reprecipitated from benzene and n-hexane, thereby obtaining monomethyl ether polyethylene glycol methoxycarbohydrazide as white powder. In the same manner, a variety of hydrazides were obtained using polyethylene glycol monomethyl ethers having average molecular weights of 550, 700, 2,000, 10,000, 15,000 and 20,000, respectively, as starting materials.

EXAMPLE 9

Monomethyl ether polyethylene glycol-4,6-dichloro-1,3,5-triazine-modified urokinase (PEG-DCT-UK)

A 0.1M phosphate buffer of pH 7.0 (2.0 ml) was added under ice-cooling to 0.61 ml of a urokinase solution (molecular weight: 54,000; 66,300 iu/ml). Thereafter, monomethyl ether polyethylene glycol-4,6-dichloro-1,3,5-triazine (the average molecular weight of the polyethylene glycol moiety: 5,000) was further added in such an amount as to bring the concentration of the triazine to 4 mM. The mixture was reacted under ice-cooling for 3 hours. After completion of the reaction, the reaction solution was transferred into a dialyzing tube, and excess triazine derivative was removed by dialysis. The dialysis was carried out under ice-cooling for 3 hours against a 0.1M phosphate buffer (pH 7.2) and then for further one hour against physiological saline. The content in the tube was then filled up to 4 ml and stored in a frozen state at $-80°$ C. The urokinase activity of the thus obtained monomethyl ether polyethylene glycol-4,6-dichloro-1,3,5-triazine-modified urokinase (PEG-DCT-UK) was determined to be 4,550 iu/ml by the fibrin plate method. Therefore, the total activity was 18,200 iu. Since the activity of the starting urokinase was 40,443 iu, an activity drop of 55% was recognized.

The above procedure was repeated except that the monomethyl ether polyethylene glycol-4,6-dichloro-1,3,5-triazine (the average molecular weight of the polyethylene glycol moiety: 5,000) was replaced by monomethyl ether polyethylene glycol-4,6-dichloro-1,3,5-triazines (the average molecular weights of the polyethylene glycol moieties: 550, 700 and 2,000, respectively), thereby obtaining modified urokinases having urokinase activities of 9,800, 10,000 and 6,500 iu/ml as determined by the fibrin plate method.

EXAMPLE 10

Monomethyl ether polyethylene glycol-4,6-dichloro-1,3,5-triazine-modified low molecular weight urokinase (PEG-DCT-L-UK)

A 0.1M phosphate buffer of pH 7.0 (4.7 ml) was added under ice-cooling to 0.2 ml of a low molecular weight urokinase solution (molecular weight: 33,000; 567,828 iu/ml). Thereafter, monomethyl ether polyethylene glycol-4,6-dichloro-1,3,5-triazine (the average molecular weight of the polyethylene glycol moiety: 5,000) was further added in such an amount as to bring the concentration of the triazine derivative to 4 mM. The mixture was reacted under ice-cooling for 3 hours. After completion of the reaction, the reaction solution was transferred into a dialyzing tube, and excess triazine derivative was removed by dialysis. The dialysis was carried out under ice-cooling for 3 hours against a 0.1M phosphate buffer (pH 7.2) and then for further one hour against physiological saline. After the dialysis, the content was filled up to 8 ml and stored in a frozen state at $-80°$ C. The urokinase activity of the thus obtained monomethyl ether polyethylene glycol-4,6-dichloro-1,3,5-triazine-modified low molecular weight urokinase (PEG-DCT-L-UK) was determined to be 10,300 iu/ml by the fibrin plate method. Thus, the total activity was 82,400 iu. Since the activity of the starting urokinase was 113,566 iu, an activity drop of 27.4% was recognized.

EXAMPLE 11

Monomethyl ether polyethylene glycol-4,6-dichloro-1,3,5-triazine-modified urokinase By repeating the procedure of Example 9 except that the concentration of each monomethyl ether polyethylene glycol-4,6-dichloro-1,3,5-triazine was changed to 0.4 mM, there were obtained, with modification degrees different from that achieved in Example 9, monomethyl ether polyethylene glycol-4,6-dichloro-1,3,5-triazine-modified urokinases (the average molecular weights of the polyethylene glycol moieties: 550, 700, 2,000 and 5,000, respectively). Their urokinase activities were 8,670, 8,900, 6,770 and 8,670 iu/ml as measured by the fibrin plate method.

EXAMPLE 12

Monomethyl ether polyethylene carbomethylazide-modified urokinase (1) To 200 mg of the monomethyl ether polyethylene glycol methoxycarbohydrazide prepared in Example 8 (the average molecular weight of the polyethylene glycol moiety: 5,000) were added under ice-cooling 1N hydrochloric acid (2 ml) and then a 0.008N aqueous solution of sodium nitrite (1 ml). The resultant mixture was stirred at room temperature for 20 minutes, and a 1N aqueous solution of sodium hydroxide (2 ml) was further added to neutralize the mixture. The resultant solution of monomethyl ether polyethylene glycol carboxymethylazide was stored at 0° C.

(2) A 0.1M phosphate buffer of pH 8.0 (3.656 ml) was added to 1 ml of a urokinase solution (molecular weight: 33,000; 45,600 iu/ml). Thereafter, 0.435 ml of the monomethyl ether polyethylene glycol carbomethylazide solution prepared in the procedure (1) above was added under mild stirring. The mixture was reacted at room temperature for 2 hours. The resulting reaction solution was then transferred into a dialyzing tube and dialyzed under ice-cooling for 4 hours against a 0.1M phosphate buffer (pH 7.2). The content was filled up to 8 ml. The resultant solution was stored in a frozen state at $-80°$ C. The urokinase activity of the thus obtained monomethyl ether polyethylene glycol carbomethylazide-modified urokinase was determined to be 7,300 iu/ml by the fibrin plate method. Compared with unmodified urokinase, an activity increase of 28% was recognized.

EXAMPLE 13

Monomethyl ether polyethylene glycol-4,6-dichloro-1,3,5-triazine-modified urokinase To 0.61 ml of a urokinase solution (molecular weight: 54,000; 101,167 iu/ml) were added under ice-cooling a 0.1M phosphate buffer of pH 7.0 (2.0 ml) and then under mild stirring monomethyl ether polyethylene glycol-4,6-dichloro-1,3,5-triazine (the average molecular weight of the polyethylene glycol moiety: 10,000). The triazine derivative was added in such an amount as to bring the concentration to 0.1 mM. The mixture was reacted for 3 hours under ice-cooling. After completion of the reaction, the reaction solution was transferred into a dialyzing tube, and excess triazine derivative was removed by dialysis. The dialysis was carried out under ice-cooling for 3 hours against a 0.1M phosphoric acid buffer added with 0.035 v/v % of ethyl amine (pH 8.0)

and then for further 2 hours against a 0.1M phosphate buffer (pH 7.2). The content was added with 3 w/v % bovine serum albumin (0.1 ml) and then filled up to 4.0 ml with a 0.1M phosphate buffer (pH 7.0). The resultant solution was stored in a frozen state at −80° C. The activity of the thus obtained monomethyl ether polyethylene glycol-4,6-dichloro-1,3,5-triazine-modified urokinase was determined to be 10,028 iu/ml by the fibrin plate method. Therefore, the total activity was 40,112 iu, and the activity drop was 35%. Similar modified urokinases were obtained by changing the concentration of the monomethyl ether polyethylene glycol-4,6-dichloro-1,3,5-triazine (the average molecular weight of the polyethylene glycol moiety: 10,000) to 0.4 and 1.0 mM, respectively. Their urokinase activities were 8,794 and 6,634 iu/ml.

Furthermore, monomethyl ether polyethylene glycol-4,6-dichloro-1,3,5-triazine (the average molecular weight of the polyethylene glycol moiety: 15,000) and urokinase were similarly reacted, thereby obtaining monomethyl ether polyethylene glycol-4,6-dichloro-1,3,5-triazine-modified urokinase (the average molecular weight of the polyethylene glycol moiety: 15,000). The activities of the modified urokinases obtained by changing the concentration of the triazine derivative to 0.1, 0.4 and 1.0 mM, respectively, were 11,388, 8,580 and 7,176 iu/ml.

EXAMPLE 14

Monostearyl ether polyethylene glycol-4,6-dichloro-1,3,5-triazine-modified urokinase To 0.2 ml of a urokinase solution (molecular weight: 54,000; 101,167 iu/ml) were added under ice-cooling a 0.1M phosphate buffer of pH 7.0 (0.66 ml) and then monostearyl ether polyethylene glycol-4,6-dichloro-1,3,5-triazine (the average molecular weight of the polyethylene glycol moiety: 3,200). The triazine derivative was added in such an amount as to bring the concentration to 2 mM. The mixture was reacted under ice-cooling for 3 hours. After completion of the reaction, the reaction solution was transferred into a dializing tube and subjected to dialysis to remove excess triazine derivative. The dialysis was carried out under ice-cooling for 4 hours against a 0.1M phosphate buffer of pH 7.2. The content was added with a 3.0% aqueous solution of bovine serum albumin (0.1 ml) and then filled up to 4.0 ml with a 0.1M phosphate buffer of pH 7.0. The resultant solution was stored in a frozen state at −80° C. The urokinase activity of the thus prepared monostearyl ether polyethylene glycol-4,6-dichloro-1,3,5-triazine-modified urokinase (the average molecular weight of the polyethylene glycol moiety: 3,200) was determined to be 2,826 iu/ml by the fibrin plate method. Since the total activity was 11,304 iu, the activity of the thus modified urokinase was 55.9% of that of the starting urokinase. The activities of the modified urokinases obtained by changing the concentration of the monostearyl ether polyethylene glycol-4,6-dichloro-1,3,5-triazine to 4, 6 and 8 mM, respectively, were 2,351, 1,430 and 1,059 iu/ml.

EXAMPLE 15

Polyethylene glycol-4-chloro-6-hydroxy-1,3,5-triazine-modified urokinase

To 1 ml of a urokinase solution (molecular weight: 54,000; 45,600 iu/ml) were added under ice-cooling a 0.05M phosphate buffer of pH 9.2 (4.0 ml) and then polyethylene glycol-4-chloro-6-hydroxy-1,3,5-triazine (2.34 mg). The average molecular weight of the polyethylene glycol moiety of the triazine derivative was 6,000. The mixture was reacted under ice-cooling for 3 hours. After completion of the reation, the reaction solution was transferred into a dialyzing tube, and excess triazine derivative was removed by dialysis. The dialysis was carried out under ice-cooling for one hour against a 0.05M phosphate buffer of pH 9.2 and then for further 3 hours against a 0.1M phosphate buffer of pH 7.2. The content was filled up to 8.0 ml with a 0.1M phosphate buffer of pH 7.2. The resultant solution was stored in a frozen state at −80° C. The urokinase activity of the thus obtained polyethylene glycol-4-chloro-6-hydroxy-1,3,5-triazine-modified urokinase (the average molecular weight of the polyethylene glycol moiety: 6,000) was determined to be 460 iu/ml by the fibrin plate method.

Similarly, there were obtained other polyethylene glycol-4-chloro-6-hydroxy-1,3,5-triazine-modified urokinases (the average molecular weights of the polyethylene glycol moieties: 4,000 and 1,000, respectively).

EXAMPLE 16

Stearoyl polyethylene glycol-4,6-dichloro-1,3,5-triazine-modified urokinase

To 0.5 ml of a urokinase solution (molecular weight: 54,000; 101,167 iu/ml) were added under ice-cooling a 0.1M phosphate buffer of pH 7.0 (1.5 ml) and then 0.05 ml of a dioxane solution of stearoyl polyethylene glycol-4,6-dichloro-1,3,5-triazine (270 mg/ml) (the average molecular weight of the polyethylene glycol moiety: 2,700). The mixture was reacted under ice-cooling for 3 hours. After completion of the reaction, the reaction solution was transferred into a dialyzing tube and subjected to dialysis to remove excess triazine derivative. The dialysis was carried out under ice-cooling for 4 hours against a 0.1M phosphate buffer of pH 7.2. The content was filled up to 5 ml with a phosphate buffer. The resultant solution was stored in a frozen state at −80° C.

The thus obtained stearoyl polyethylene glycol-4,6-dichloro-1,3,5-triazine-modified urokinase was found, a result of the urokinase activity measurement by the fibrin plate method, to have an activity of 106% of that of the starting urokinase.

Other stearoyl polyethylene glycol-4,6-dichloro-1,3,5-triazine-modified urokinases having different modification degrees were obtained by reaction with urokinase using a dioxane solution of stearoyl polyethylene glycol-4,6-dichloro-1,3,5-triazine (270 mg/ml) in amounts of 0.1 and 0.2 ml, respectively. The average molecular weight of the polyethylene glycol moiety of the triazine derivative was 2,700. The thus prepared modified urokinases had activities of 106 and 101% of that of the starting urokinase.

EXAMPLE 17

Polypropylene glycol-4-chloro-6-hydroxy-1,3,5-triazine-modified urokinase

To 0.5 ml of a urokinase solution (molecular weight: 54,000; 101,167 iu/ml) were added under ice-cooling a 0.1M phosphate buffer of pH 7.0 (1.5 ml) and then 0.05 ml of a dioxane solution of the polypropylene glycol-4-chloro-6-hydroxy-1,3,5-triazine (100 mg/ml) obtained in Example 6. The average molecular weight of the polypropylene glycol moiety of the triazine derivative was 1,000. The mixture was reacted under ice-cooling for 3 hours. After completion of the reaction, the reaction solution was transferred into a dialyzing tube and subjected to dialysis to remove excess triazine derivative. The dialysis was carried out under ice-cooling for 4 hours against a 0.1 M phosphate buffer of pH 7.2. The content was filled up to 5 ml with a phosphate buffer and then stored in a frozen state at −80° C. The thus obtained polypropylene glycol-4-chloro-6-hydroxy-1,3,5-triazine-modified urokinase was found to retain an activity of 96.4% of that of the starting urokinase by the fibrin plate method.

Other polypropylene glycol-4-chloro-6-hydroxy-1,3,5-triazine-modified urokinases having different modification degrees were similarly obtained by using a dioxane solution of polypropylene glycol-4-chloro-6-hydroxy-1,3,5-triazine (100 mg/ml) in amounts of 0.1 and 0.2 ml, respectively. The average molecular weight of the polypropylene glycol moiety of the triazine derivative was 1,000. The modified urokinases showed activities of 99.3 and 106.8% in comparison with that of the starting unmodified urokinase.

EXAMPLE 18

Polypropylene glycol-4-chloro-6-hydroxy-1,3,5-triazine-modified urokinase

Polypropylene glycol-4-chloro-6-hydroxy-1,3,5-triazine-modified urokinases having different modification degrees were obtained exactly in the same manner as in Example 3 with use of a dioxane solution containing 400 mg/ml of the polypropylene glycol-4-chloro-6-hydroxy-1,3,5-triazine obtained in Example 7 in amounts of 0.05, 0.1 and 0.2 ml, respectively. The average molecular weight of the polyethylene glycol moiety of the triazine derivative was 4,000. Their urokinase activities were found to be 89.7, 100.0 and 98.9% of the that of the starting urokinase by the fibrin plate method.

EXAMPLE 19

Optimum pH for modified urokinase as measured in terms of amidase activity

PEG-DCT-UK obtained in Example 9 and unmodified urokinase were each diluted with physiological saline containing 0.1% human albumin to obtain two solutions of 167 iu/ml. Each of the solutions were divided into portions of 0.3 ml which were added with 50 mM tris-HCl buffers of different pH levels (each 1.0 ml) and then with a synthetic substrate S-2444 (pyrGlu-Gly-Arg-p-nitroanilide made by Kabi Corporation). The resultant mixtures were incubated at 37° C. for 10 minutes. The reactions were then stopped by the addition of 30% acetic acid. Their absorbance was measured at 405 nm. As a result, the optimum pH levels for PEG-DCT-UK and unmodified urokinase were 8.2 and 8.5, respectively, as measured in terms of the amidase activity when the synthetic substrate S-2444 was employed. The results are shown in FIG. 1.

The optimum pH levels for PEG-DCT-L-UK obtained in Example 4 and unmodified low molecular weight urokinase were determined similarly in terms of the amidase activity and were found to be 8.2 and 8.4, respectively. The results are shown in FIG. 2.

EXAMPLE 20

Stability of modified urokinase at room temperature

PEG-DCT-UK obtained in Example 9 was diluted with either a Ringer solution or physiological saline to a concentration of 105.3 iu/ml. For the sake of comparison, unmodified urokinase was also diluted with either a Ringer solution or physiological saline to a concentration of 76.1 iu/ml. 3.5 ml of each of the thus diluted solutions was allowed to stand at room temperature (27° C.) for 6 hours. The residual urokinase activity was periodically measured by the fibrin plate method until such time that 6 hours elapsed. The extent of activity loss of the modified urokinase according to the invention was by far smaller than that of unmodified urokinase. The results are shown in FIG. 3.

EXAMPLE 21

Stability of modified urokinase against freezing and thawing processing

PEG-DCT-L-UK obtained in Example 10 was diluted with physiological saline to a concentration of 200 iu/ml. For the sake of comparison, unmodified low molecular weight urokinase was diluted with physiological saline to a concentration of 200 iu/ml. Each of the thus diluted solutions was frozen to −80° C. and subsequently thawed at room temperature. The freezing and thawing operations were repeated 0, 2, 4 and 6 times. The residual urokinase activity was measured using a synthetic substrate S-2444 (made by Kabi Corporation). The extent of activity loss of the modified urokinase according to the invention was extremely low as compared with that of unmodified low molecular weight urokinase. The results are shown in FIG. 4.

EXAMPLE 22

Eight healthy male rabbits (Japanese white) each having a body weight of 2.6–3.1 kg were divided into two groups. One group was dosed with 8,000 iu/kg of PEG-DCT-UK and the other with 8,000 iu/kg of unmodified urokinase, both through the ear veins. Blood was collected from the ear veins before the dosage and at the time of 1, 2 and 4 hours after the dosage. Blood samples were added with a sodium citrate solution to separate plasma. After wash-out of the modified and unmodified urokinases for 18 days, the two groups were crossed with each other, and similar experiments were carried out to take plasma samples. A part of each of the plasma samples thus obtained was separated and subjected to affinity column chromatography using Lysine Sepharose 4B, thereby obtaining a plasmin inhibitor fraction (fraction $F_1$) and a plasmin and plasminogen fraction (fraction $F_3$). Changes in the amount of the plasmin inhibitor in the fraction $F_1$ along the passage of time were determined by adding plasmin to the fraction $F_1$ and measuring the amount of residual plasmin which was not adversely affected by the inhibitor, with a synthetic substrate S-2251 (made by Kabi Corporation). The plasmin inhibitor from the PEG-DCT-UK-administered group showed its apparent decrease and slower recovery. In the unmodified urokinase-administered group, the decrease in the plasmin inhibitor was rather less, and its time course changes were not made clear. The results are shown in FIG. 5.

On the other hand, the amount of plasminogen in the fraction $F_3$ was determined by adding urokinase to the fraction $F_3$ to produce plasmin and measuring the amount of the thus produced plasmin by a synthetic substrate S-2251. In the PEG-DCT-UK-administered group, plasminogen decreased to about 50% after 2 hours and thereafter recovered gradually. However, in the unmodified urokinase-administered group, plasminogen decreased up to about 65% after one hour but did not proceed to decrease any further. There was observed a tendency of plasminogen being recovered even 2 hours after the dosage. The results are illustrated in FIG. 6.

Furthermore, a part of each plasma was sampled and treated with an acid to pH 5.2 so as to deactivate the inhibitor therein. It was then neutralized, and the amount of plasminogen present in the acid treated plasma was measured by adding urokinase to the acid treated plasma to produce plasmin and measuring the amount of the thus produced plasmin using a synthetic substrate S-2251. In the PEG-DCT-UK-administered group, plasminogen decreased to about 70% after 2 hours but showed its gradual recovery thereafter. In the unmodified urokinase-administered group, however, the amount of plasminogen was decreased to about 84% after one hour but was not decreased any further. Thereafter, the amount of plasminogen was increased gradually. The results are also shown in FIG. 6. Incidentally, no plasmin activity was detected from the fraction $F_3$.

EXAMPLE 23

Lyophilized product suitable for the preparation of injectable formulations

The PEG-DCT-UK solution obtained in Example 9 was concentrated by a membrane filter (Amicon Gel: trademark) and then added with physiological saline and a 0.05M phosphate buffer. The resultant mixture was filtered aseptically using a membrane filter. The filtrate was poured in portions into sterilized vials and then lyophilized. The fibrinolytic activity of the lyophilized product of PEG-DCT-UK suitable for the preparation of injectable formulations was found to be 57,000 iu/vial by the fibrin plate method.

EXAMPLE 24

Lyophilized product suitable for the preparation of injectable formulations

The PEG-DCT-UK solution obtained in Example 9 was concentrated by a membrane filter (Amicon Gel: trademark) and then added with physiological saline. The resultant mixture was filtered aseptically using a membrane filter. The filtrate was poured in portions into sterilized vials and then lyophilized. The fibrinolytic activity of the thus obtained lyophilized product of PEG-DCT-UK suitable for the preparation of injectable formulations was found to be 67,000 iu/vial by the fibrin plate method.

The invention now being fully described, it will be apparent to one of ordinary skill in the art that many changes and modifications can be made thereto without departing from the spirit or scope of the invention as set forth herein.

What is claimed is:

1. A derivative of a human-originated non-immunogenic plasminogen activator, comprising at least one polyalkylene glycol chemically bonded with at least one coupling agent to amino acid side chains of said plasminogen activator, wherein said polyalkylene glycol has a molecular weight in the range of 200–20,000 and is unsubstituted or is substituted with one or more alkyl or one or more alkanoyl groups.

2. The derivative as claimed in claim 1, wherein said plasminogen activator is urokinase.

3. The derivative as claimed in claim 1, wherein said polyalkylene glycol is selected from the group consisting of an unsubstituted polyethylene glycol, a polyethylene glycol substituted with one or more alkyl or one or more alkanoyl groups, an unsubstituted polypropylene glycol, or a polypropylene glycol substituted with one or more alkyl or one or more alkanoyl groups, or a mixture thereof.

4. The derivative as claimed in claims 1 or 3, wherein said polyalkylene glycol is a polyethylene glycol monoalkyl ether.

5. The derivative as claimed in claims 1 or 3, wherein said polyalkylene glycol is a polypropylene glycol.

6. The derivative as claimed in claim 1, wherein said polyalkylene glycol has a molecular weight in the range of 500–10,000.

7. The derivative as claimed in claim 1, wherein said coupling agent is a cyanuric halide.

8. Monomethyl ether polyethylene glycol-4,6-dichloro-1,3,5-triazine-modified urokinase, whose polyethylene glycol moiety has an average molecular weight of 5,000.

9. Polypropylene glycol-4-chloro-6-hydroxy-1,3,5-triazine-modified urokinase, whose polypropylene glycol moiety has an average molecular weight of 4,000.

10. A process for preparing a derivative of a human-originated non-immunogenic plasminogen activator, which comprises reacting a coupled product of at least one polyalkylene glycol and at least one coupling agent with a plasminogen activator, wherein said polyalkylene glycol has a molecular weight in the range of 200–20,000 and is unsubstituted or is substituted with one or more alkyl or one or more alkanoyl groups.

11. The process as claimed in claim 10, wherein said plasminogen activator is urokinase.

12. The process as claimed in claim 10, wherein said coupled product and said plasminogen activator are reacted under such conditions that the latter activator does not lose its physiological activity.

13. A thrombolytic agent comprising a derivative of a human-originated non-immunogenic plasminogen activator as claimed in claim 1.

14. The process as claimed in claim 12, wherein said conditions comprise reacting said coupled product and said plasminogen activator at a temperature in the range of 0° C. to room temperature at a pH in the range of 2 to 10, whereby said plasminogen activator does not lose its physiological activity.

15. A derivative of a human-originated non-immunogenic plasminogen activator, produced by a process which comprises reacting a coupled product of at least one polyalkylene glycol and at least one coupling agent with a plasminogen activator, wherein said polyalkylene glycol has a molecular weight in the range of 200–20,000 and is unsubstituted or is substituted with one or more alkyl or one or more alkanoyl groups.

16. The derivative as claimed in claim 15, wherein said coupled product and said plasminogen activator are reacted under conditions that the latter activator does not lose its physiological activity.

17. The derivative as claimed in claim 15, wherein said plasminogen activator is urokinase.

* * * * *

REEXAMINATION CERTIFICATE (574th)
United States Patent [19]
Shimizu et al.

[11] B1 4,495,285
[45] Certificate Issued Sep. 23, 1986

[54] PLASMINOGEN ACTIVATOR DERIVATIVES

[75] Inventors: Kimihiro Shimizu, Saitama; Tsuguji Nakahara, Tokyo; Taketoshi Kinoshita, Saitama, all of Japan

[73] Assignee: Nippon Chemiphar Co., Ltd., Tokyo, Japan

Reexamination Request:
No. 90/000,821, Jul. 12, 1985

Reexamination Certificate for:
Patent No.: 4,495,285
Issued: Jan. 22, 1985
Appl. No.: 437,009
Filed: Oct. 27, 1982

[30] Foreign Application Priority Data

Oct. 30, 1981 [JP] Japan ................. 56-172908

[51] Int. Cl.$^4$ ............ C12N 9/72; C12N 9/48; C12N 11/06
[52] U.S. Cl. ................. 435/215; 435/212; 435/181
[58] Field of Search .............. 435/181, 212, 215

[56] References Cited

U.S. PATENT DOCUMENTS

4,179,337  12/1979  Davis et al. .................. 435/181

OTHER PUBLICATIONS

*The Merck Index*, 9th edition, Merck & Co., Inc., Rahway, N.J. (1976).

Abuchowski, A. et al., "Preparation and Properties of Polyethylene Glycol-Trypsin Adducts," Biochem. and Biophys. Acta. 578: 41-46 (1979).

Savoca, K. et al. "Preparation of a Non-Immunological Arginase by the Covalent Attachment of Polyethylene Glycol," Biochem. and Biophys. Acta. 578: 47-53.

Savoca, K. et al. "Immunological and Cytotoxical Effects of Beef Liver Arginase Modified by Attachment of Polyethylene Glycol," Fed. Am. Soc. for Exp. Biol. Proceedings, Abstract No. 5021 (Mar. 1979). (Savoca II).

Pyatak, P. et al., "Preparation of a Polyethylene Glycol: Superoxide Dismustase Adduct, and an Examination of its Blood Circulating Life and Antiinflammatory Activity," Res. Comm. Chem. Pathol. Pharmacol. 29(1): 113-127 (1980).

King, T. P. et al., "Immunological Properties of Conjugates of Ragweed Pollen Antigen E with Methoxypolyethylene Glycol or a Copolymer of D-Glutamic Acid and D-Lysine," J. Exp. Med. 149: 424 (Feb. 1979).

Lee, W. Y. et al., "Suppression of Reaginic Antibodies with Modified Allergens," Int. Archs. Allergy appl. Immun. 56: 193-206 (1978).

Weider, K. et al., "Some Properties of Polyethylene Glycol: Phenylalanine Ammonia-Lyase Adducts," J. Biol. Chem. 254(24): 12579-12587 (1979).

Stephen Davis et al., "Hypouricaemic Effect of Polyethylene Glycol Modified Urat Oxidase," Lancet, pp. 281-283, (Aug. 8, 1981).

Ajisaka et al., "Modification of Human Hemoglobin with Polyethylene Glycol: A new Candidate for Blood Substitute," Biochem. and Biophys. Res. Comm. 97: 1076-1081 (Dec. 16, 1980).

Encyclopedia of Chemical Technology, Blood, Coagulents and Anticoagulants, vol. 4 (1985 supplement) pp. 19-21.

Innerfield et al., J.A.M.A., vol. 152, No. 7, pp. 597-605, Jun. 13, 1953.

Marino, "A Clinical Evaluation of Parenteral Trypsin in Thrombophlebitis" in AM & CT, vol. V, No. 9, Sep. 1958, pp. 553-558.

Innerfield et al., J. Clinical Investigation, vol. 31, 1049-1055 (1952).

Seligman, Angiology, vol. 6, 208-211 (1955).

Glazer et al., Journal of Biological Chemistry, vol. 237, No. 6, 1832-1838 (Jun. 1962).

Alkjaersig et al., Journal of Biological Chemistry, vol. 233, No. 1, pp. 86-90 (1958).

Lewis et al., American Journal of Physiology, vol. 170, 636-641 (1952).

*Primary Examiner*—Lionel M. Shapiro

[57] ABSTRACT

A derivative of a human-originated non-immunogenic plasminogen activator is disclosed which comprises at least one polyalkylene glycol attached with at least one coupling agent to amino acid side chains of said plasminogen activator, said polyalkylene glycol having a molecular weight of 200-20,000 and optionally containing one or more alkyl and/or alkanoyl groups as substituents. Also disclosed are a process for producing such derivative and a thrombolytic agent containing such derivative.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-17 is confirmed.

* * * * *